United States Patent [19]

Rosenberg

[11] 4,153,700

[45] May 8, 1979

[54] TREATMENT OF THE ACUTE AFTER-EFFECTS RESULTING FROM ALCOHOL INGESTION

[75] Inventor: Carl S. Rosenberg, Chicago, Ill.

[73] Assignee: Lake Shore Roentgenology Ltd., Chicago, Ill.

[21] Appl. No.: 805,595

[22] Filed: Jun. 10, 1977

Related U.S. Application Data

[63] Continuation-in-part of Ser. No. 608,103, Aug. 27, 1975, which is a continuation-in-part of Ser. No. 111,077, Jan. 29, 1971, abandoned.

[51] Int. Cl.$^2$ ............................................. A61K 31/48
[52] U.S. Cl. ..................................... 424/261; 424/250
[58] Field of Search ................................ 424/261, 250

[56] References Cited

U.S. PATENT DOCUMENTS 3,917,839  11/1975  Schneider et al. .................... 424/261

FOREIGN PATENT DOCUMENTS 1011112  11/1965  United Kingdom ...................... 424/261
1180120  2/1970  United Kingdom ...................... 424/261

OTHER PUBLICATIONS

*Headache*, Wolff, 2nd Ed. (1963), pp. 178-179, Oxford Univ. Press.
*The Merck Index*, Eighth Ed., p. 316, 1968, Merck & Co. Inc., Rahway, N.J.

*Primary Examiner*—Frederick E. Waddell

[57] ABSTRACT

A composition and method for the prevention of alcohol-induced thirst and/or fatigue and/or nausea, as well as other less common after-effects resulting from excess alcohol ingestion wherein the composition is formulated to contain a dibenzocycloheptatriene derivative such as cyproheptadine and a lysergic acid derivative such as ergotamine. It has been found that these two classes of antagonists of 5-hydroxytryptamine act synergistically in minimizing or preventing an acute inflammatory reaction otherwise resulting from ingestion of excess alcohol.

2 Claims, No Drawings

TREATMENT OF THE ACUTE AFTER-EFFECTS RESULTING FROM ALCOHOL INGESTION

This is a continuation-in-part of copending application Ser. No. 608,103, filed Aug. 27, 1975, which in turn is a continuation application-in-part of the then copending application Ser. No. 111,077, filed Jan. 29, 1971, now abandoned.

This invention relates to the prevention of the acute post-alcoholic intoxication state, commonly called the alcohol "hangover". A "hangover" results from ingesting a relatively excessive quantity of alcohol, a term understood to refer to alcoholic beverages as well as any particular alcohol found in such beverages.

More particularly, the method of the invention is concerned with the prevention of alcohol-induced thirst and/or fatigue and/or nausea by administering to a person compounds which are relatively safe and effective, competitive antagonists of 5-hydroxytryptamine (5-HT).

When a person ingests alcohol, approximately 2–10% of the ethyl alcohol contained in the beverage is excreted from the body unchanged in expired air and in the urine. The remainder of the alcohol is either oxidized or is used in synthesizing cholesterol.

Without limiting the invention as to theory, it is believed that enzymatic oxidation of an alcohol, by the enzyme alcohol dehydrogenase-linked nicotinamide-adeninedinucleotide (NAD), the alcohol is converted to its corresponding aldehyde. This reaction occurs at a nearly constant rate, independent of the quantity of alcohol present in the body.

Each aldehyde should then undergo enzymatic oxidation to its corresponding acid by the enzyme aldehyde dehydrogenase-linked NAD. The latter oxidation may not occur at a uniform rate. It can be adversely affected either by an aldehyde directly inhibiting the oxidation of; the reduced co-enzyme $NADH_2$; or, but two or more aldehydes competitively inhibiting the aldehyde dehydrogenase-linked NAD. Either effect will cause an accumulation of aldehyde to occur.

A rapid accumulation of aldehyde, within several minutes, occurs in those persons who take disulfiram; which produces the so-called "aldehyde reaction". A more prolonged accumulation of aldehyde, over several hours, is believed to provoke an acute type of inflammatory reaction which is though to be the basic cause of the acute post-alcoholic intoxication state.

An acute type of inflammatory reaction is a tissue's nonspecific defensive mechanism against any sudden appearance of a noxious substance. It is believed that an acute type of inflammatory process is initiated whenever 5-HT is released within the tissues of an area involved with a noxious substance. The unbound 5-HT is now able to cause spasm of smooth muscle cells by occupying specific and critical receptor-sites on these cells; most significantly, those smooth muscle cells in the wall of post-capillary venules within the area involved by the noxious material. An acute type of inflammatory process, therefore, is the result initiated by the unbound 5-HT. The foregoing is a somewhat simplified description, but is sufficient to facilitate an understanding of the invention.

In my copending application Ser. No. 608,103, there is described a method for treating alcohol-induced thirst, fatigue and/or nausea in which an effective amount of an antagonist of 5-HT is administered prior to the onset of the acute post-alcoholic intoxication state. As is described in my copending application, preferred antagonists of 5-HT include cyproheptadine or certain lysergic derivatives. In addition to treating thirst, fatigue and/or nausea, the method described and claimed in my copending application is also effective in preventing or substantially minimizing other, less common clinical manifestations of the acute post-alcoholic intoxication state such as malaise, insomnia, drowsiness, anorexia, headache, vertigo, feelings of guilt, depression and anxiety.

It has now been found that the effectiveness of antagonists of 5-HT in preventing the acute after-effects of the post-alcoholic intoxication state, notably thirst, fatigue and/or nausea, can be further improved by the use of, in combination, (1) a dibenzocycloheptatriene derivative of the formula

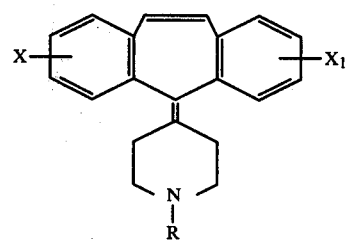

wherein X and $X_1$ are each selected from the group consisting of hydrogen, halogen, lower alkyl and lower alkoxy and R is selected from the group consisting of hydrogen, lower alkyl, lower alkenyl, hydroxy lower alkyl, methane sulfonyloxy lower alkyl and dilower alkyl amino lower alkyl, and (2) a pharmaceutically-acceptable lysergic acid derivative having the formula:

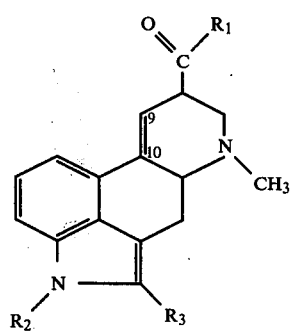

wherein $R_1$ is selected from the group consisting of mono- and dialkylamino, mono-(hydroxyalkyl)amino, di-(hydroxyalkyl) amino, said alkyl and alkylene groups containing from 1 to 4 carbon atoms and the substituent:

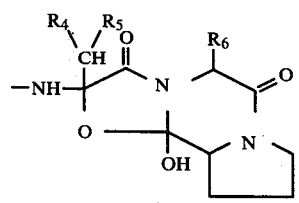

wherein $R_4$ and $R_5$ are each selected from the group consisting of H and methyl and $R_6$ is selected from the group consisting of benzyl, isopropyl and isobutyl;

$R_2$ is selected from the group consisting of H, alkyl, said alkyl containing from 1 to 4 carbon atoms;

$R_3$ is selected from the group consisting of H, Cl, Br, F and I; and the pharmaceutically-acceptable acid-addition salts thereof. These compounds can be incorporated with an inert pharmaceutical carrier or diluent.

The relative proportions of the dibenzocycloheptatriene derivative and the lysergic acid derivative ranges from a weight ratio of 1–12 parts by weight of the lysergic acid derivative to the dibenzocycloheptatriene, and preferably 2–8 parts by weight of the lysergic acid derivative for each part by weight of the dibenzocycloheptatriene derivative. Best results are usually achieved when the weight ratio of lysergic acid to dibenzocycloheptatriene derivative is 1 to 4.

The dibenzocycloheptatriene derivatives used in the practice of this invention are known to those skilled in the art, and are described in detail in U.S. Pat. No. 3,014,911, the disclosure of which is incorporated herein by reference. The preferred compound is the derivative having the formula:

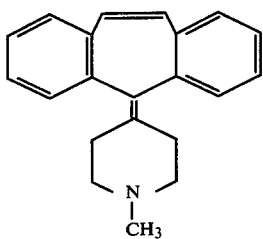

known generically as cyproheptadine.

The preferred lysergic acid derivatives for use in the practice of this invention are those in which $R_2$ and $R_3$ are hydrogen. Examples of this type of compound include ergotamine, ergonovine and methyl ergonovine. Other preferred compounds include those wherein $R_2$ is an alkyl group, such as 1-methyl ergotamine, 1-methyl-ergonovine and 1-methyl-methylergonovine. Other preferred compounds used in the practice of this invention are those in which the 5-membered ring in the 9 and 10 positions are saturated, as well as those compounds wherein $R_3$ is a halide such as 2-bromoergotamine.

It is known that the physiologically-active members of the lysergic acid derivatives are the dextro stereoisomers, arbitrarily defined according to the spacial arrangement about the asymmetric carbon atoms in the 5 and 8 positions. The dextro form, whether it is an enantiomorph or a di-astereoisomer, rotates polarized-like in a counterclockwise direction. Hence, the physiologically-active compounds are the livo-rotary isomers of dextro lysergic acid, described as D(-) lysergic acid or as D(1) lysergic acid derivatives. While the structures drawn herein do not refer to configuration or physical properties, it will be understood that the livo-rotary dextro isomer is the one employed in the practice of this invention.

The combination of the dibenzocycloheptatriene derivative and the lysergic acid derivative can be administered in accordance with established methods, oral and sublingual methods being preferred. The effective dosage generally ranges from 0.1 mg to 10 mgs of the combination.

The layman frequently considers the headache as the unique determining factor as to whether one does or does not have a "hangover". That assumption is false because a headache occurs only 35–40% of all acute post-alcoholic intoxication states. Even if one were to suffer from a headache, the complete absence of alcohol-induced thirst, fatigue and nausea categorically rules out the acute post-alcoholic intoxication state as defined above.

The acute post-alcoholic intoxication state reaches its full intensity several hours after a person had been drinking; when the blood level of alcohol has returned to normal. At this time, administering an antagonist of 5-HT can have no effect. The reason being that the receptor-sites would then be occupied by 5-HT, which would have initiated an acute type of inflammatory reaction.

Antagonists of 5-HT can only prevent an acute type of inflammatory process by occupying the receptor-sites prior to their occupation by 5-HT. The antagonists do not cause significant, if any, spasm of the above-mentioned smooth muscle cells. Therefore, it is mandatory to know that a release of 5-HT is to occur within the next several hours in order to receive the therapy at the proper time. Otherwise, a person would awaken during the full intensity of an acute post-alcoholic intoxication state. Thus, to be effective, antagonists of 5-HT administered in accordance with the practice of this invention should be given prior to or during the early onset of the acute after-effects of alcohol ingestion.

An antagonist cannot dislodge 5-HT from a receptor-site; nor can 5-HT dislodge an antagonist from a receptor-site. This is critically important, in that they compete for an empty receptor-site, but only the first to arrive is able to take possession of said empty receptor-site.

As stated above, aldehydes inhibit and compete for the same enzyme, i.e., aldehyde dehydrogenase-linked NAD. Were the enzyme not adversely involved, it would rapidly promote the oxidation of aldehydes to their corresponding acids in order to eliminate them from the body as end-products of the metabolism of alcohol. Thusly, an acute type of inflammatory reaction could not occur, since there would be no aldehyde accumulation to irritate tissue, which causes 5-HT to be released.

In some ways, it is presumed, the reaction $$NADH_2 + O = NAD + H_2O$$

is inhibited. As a result of this inhibition, there is produced an elevated level of aldehyde in the blood, and later, in the cerebrospinal fluid. This is the result of having ingested a relatively excessive amount of alcohol.

To compare the various headaches, the vascular headaches and the migraine with the acute post-alcoholic intoxication state can be shown to be a priori incorrect.

Alcohol-induced thirst and/or fatigue and/or nausea are the sine qua non of the acute post-alcoholic intoxication state, whereas cephalagia alone is the sine qua non of the various headaches, the vasular headaches and the migraine.

In order to fully understand the headache syndrome as a separate group of entities, neither related to nor similar to the acute post-alcoholic intoxication state, it becomes expedient to compare them.

Several observations will be stated. Each will first present a single and simple statement thought to have objective reality concerning the various headaches, the vascular headaches and the migraine; and each in turn will be countered by a statement presently accepted as having objective reality concerning the acute post-alcoholic intoxication state:

Cephalagia, by definition, must exist in order for the various headaches, the vascular headaches and the migraine to be present, whereas cephalagia is not an essential component of the acute post-alcoholic intoxication state;

Without cephalagia, the various headaches, the vascular headaches and the migraine cannot, by definition, exist, whereas the acute post-alcoholic intoxication state occurs even though cephalagia is absent 65 to 70% of the time;

Cephalagia is the sine qua non of the various headaches, the vascular headaches and the migraine, whereas cephalagia is present in only 30 to 35% of all acute post-alcoholic intoxication states;

Thirst, per se, is not a symptom of the various headaches, the vascular headaches or the migraine, whereas thirst and/or fatigue and/or nausea, solely induced by alcohol ingestion, must be present in order for the acute post-alcoholic intoxication state to be present. They are the sine qua non of the acute post-alcoholic intoxication state, as it is defined in the specification;

Thirst, per se, is not a manifestation of the various headaches, the vascular headaches or the migraine unless it is secondary to the inability to retain fluids because of severe and continued vomiting, whereas the absence of thirst, as well as fatigue and nausea, after alcohol ingestion, rules out the presence of the acute post-alcoholic intoxication state, as it is defined in the specification;

Fatigue, per se, does not occur in the various headaches, the vascular headaches and the migraine, except after many hours and days of suffering, whereas fatigue occurs in 75 to 80% of the acute post-alcoholic intoxication state, and is probably present at the onset;

An aura often occurs minutes before the cephalagia begins in the various headaches, the vascular headaches and the migraine, whereas there is no aura involved in the acute post-alcoholic intoxication state;

Pallor often occurs during the various headaches, the vascular headaches and the migraine, whereas there is no pallor in the acute post-alcoholic intoxication state;

Sweating often occurs during the various headaches, the vascular headaches and the migraine, whereas there is no sweating during the acute post-alcoholic intoxication state;

Flushing often occurs during the various headaches, the vascular headaches and the migraine, whereas no flushing occurs during the acute post-alcoholic intoxication state;

Photophobia is very common during the various headaches, the vascular headaches and the migraine, whereas photophobia is not common in the acute post-alcoholic intoxication state;

Attacks of various headaches, vascular headaches, and migraines often occur in a quasi-random manner, although they are predictable to some extent, whereas the acute post-alcoholic intoxication state occurs hours following ingestion of alcohol and its intensity is usually dependent upon the amount and type of alcohol previously consumed;

An attack of various headaches, the vascular headaches and the migraine can begin at any time, whereas the acute post-alcoholic intoxication state is almost always present upon awakening in the morning, at which time the acute post-alcoholic intoxication state is at its highest intensity;

The various headaches, the vascular headaches and the migraine reach their full intensity usually over a period of several hours, whereas the signs and symptoms of the acute post-alcoholic intoxication state are immediately realized upon awakening, at which time they are at their highest intensity;

The various headaches, the vascular headaches and the migraine have unpredictable durations, lasting from several minutes to several days, whereas the duration of the acute post-alcoholic intoxication state is limited to 1 to 12 hours 98% of the time, and a headache need not be present;

Mental depression is not an essential symptom of the various headaches, the vascular headaches or the migraine, although it can occur after several hours as the patient develops an acute reactive depression, whereas mental depression is often present in the acute post-alcoholic intoxication state. It also is present at the beginning, not several hours later;

Feelings of guilt are not present during the various headaches, the vascular headaches and the migraine, whereas feelings of guilt are very often present during the acute post-alcoholic intoxication state;

A specific etiology of the various headaches, the vascular headaches and the migraine are less than fully understood by those skilled in the art. Numerous explanations have been published in the literature, and these have been acknowledged by the art, whereas the causal factor of the acute post-alcoholic intoxication state is well known and obvious to one skilled in the art as well as to the laity. The causal factor is also unique and singular, i.e., excessive ingestion of alcohol;

The pathophysiology of the various headaches, the vascular headaches and the migraine is understood to be the dilitation of cranial and/or intracranial arteries, and nothing more, whereas the pathophysiology of the acute post-alcoholic intoxication state is, and may remain, essentially unknown by those who are skilled in the art;

The dilitation of certain arteries is known to be a cause of cephalagia. The dilitation has been demonstrated to respond favorably to the administration of ergotamine, whereas significant vascular dilitation, while present during the period of acute alcoholic intoxication, has not been observed during the acute post-alcoholic intoxication state, nor has ergotamine or other vasoconstrictors demonstrated any clinical effectiveness if administered during a "hangover" headache;

Inhibition of aldehyde dehydrogenase-linked NAD is absent during the various headaches, the vascular headaches and the migraine, whereas aldehyde dehydrogenase-linked NAD is markedly inhibited during the acute post-alcoholic intoxication state;

No accumulation of endogenous aldehyde occurs during the various headaches, the vascular headaches and the migraine, whereas a marked accumulation of aldehyde is known to the art to occur during the acute post-alcoholic intoxication state;

There is no significant increase or decrease in the turnover of neuroamines, such as 5-HT in the various headaches, the vascular headaches and the migraine, whereas there is a marked increase in the turnover of neuroamines, such as 5-HT during the acute post-alcoholic intoxication states;

5-HT metabolism is not affected either before, during or after an attack of the various headaches, the vascular headaches and the migraine, whereas 5-HT metabolism is markedly affected during the acute post-alcoholic intoxication state;

The urinary excretion of 5-hydroxyindole acetic acid (5-HIAA) is unchanged during the various headaches, the vascular headaches and the migraine, whereas there is a marked increase in the urinary excretion of 5-hydroxytryptophol during the acute post-alcoholic intoxication state. This is secondary to inhibition of aldehyde dehydrogenase-linked NAD;

The treatment of the various headaches, the vascular headaches and the migraine is well known and accepted by the art, and it is based on scientific investigation, whereas the art does not consist of any method of preventing the acute post-alcoholic intoxication state. There is symptomatic therapy as well as "folk-remedies"; none are effective. They are used for relief of symptoms during the acute post-alcoholic intoxication state. The art does not teach a method of preventing the "hangover" after the alcohol has been ingested.

Having described the basic concepts of the invention, reference is now made to the following examples, which are provided by way of illustration and not of limitation, of the practice of the invention.

EXAMPLE 1

This example illustrates the preferred formulation embodying the features of this invention.

The pharmaceutical composition was formulated to contain 0.1 mg of ergotamine tartrate and 4 mg of cyproheptadine. The two substances were blended together and then administered orally to a series of individuals who had each consumed a sufficient quantity of alcoholic beverage to cause him to feel lethargic and to admit to being intoxicated and apprehensive concerning the possibility of acute after-effects on the following morning.

It was found that the persons receiving the medication had negligible symptoms of an acute post-alcoholic intoxication state on the next day.

EXAMPLE 2

Using the procedure described in Example 1, the composition was formulated as follows:

|  | Parts by Weight |
| --- | --- |
| Ergotamine tartrate | 2 |
| Cyproheptadine | 4 |
| Inert Carrier | 100 |

It will be understood that various changes and modifications can be made in the details of formulation and use without departing from the spirit of the invention, especially as defined in the following claims.

I claim:

1. A composition for use in the treatment of the acute after effects resulting from alcohol ingestion consisting essentially of ergotamine tartrate and cyproheptadine, the ergotamine tartrate being present in a weight ratio within the range 1 to 12 parts by weight per part by weight of cyproheptadine.

2. A method for prevention of alcohol induced thirst, fatigue and/or nausea comprising administering to a person who has ingested alcohol an effective amount of a composition consisting essentially of ergotamine tartrate and cyproheptadine, the ergotamine tartrate being present in a weight ratio within the range 1 to 12 parts by weight per part by weight of cyproheptadine.

* * * * *